(12) United States Patent  
Yodfat et al.

(10) Patent No.: US 9,138,531 B2  
(45) Date of Patent: Sep. 22, 2015

(54) DEVICE, A SYSTEM AND A METHOD FOR IDENTIFICATION/AUTHENTICATION OF PARTS OF A MEDICAL DEVICE

(75) Inventors: Ofer Yodfat, Modi'in (IL); Avihoo P. Keret, Kfar Vradim (IL)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1274 days.

(21) Appl. No.: 12/995,068

(22) PCT Filed: May 27, 2009

(86) PCT No.: PCT/IL2009/000533  
§ 371 (c)(1),  
(2), (4) Date: Jan. 26, 2011

(87) PCT Pub. No.: WO2009/144726  
PCT Pub. Date: Dec. 3, 2009

(65) Prior Publication Data  
US 2011/0118694 A1     May 19, 2011

Related U.S. Application Data

(60) Provisional application No. 61/057,088, filed on May 29, 2008.

(51) Int. Cl.  
*A61M 5/14* (2006.01)  
*A61M 5/142* (2006.01)  
(Continued)

(52) U.S. Cl.  
CPC ......... *A61M 5/1413* (2013.01); *A61M 5/14248* (2013.01); *A61B 5/14532* (2013.01); *A61M 5/1723* (2013.01); *A61M 2005/14252* (2013.01); *A61M 2005/14268* (2013.01); *A61M 2005/14573* (2013.01); *A61M 2205/273* (2013.01); *A61M2205/276* (2013.01); *A61M 2205/6018* (2013.01); *A61M 2205/6054* (2013.01); *A61M 2205/6072* (2013.01); *G06F 19/3406* (2013.01)

(58) Field of Classification Search  
CPC ............ A61M 5/1413; A61M 5/1426; A61M 2005/14248; A61M 2005/14252; A61M 2005/14268; A61M 2005/14573; A61M 2205/273; A61M 2205/276; A61M 2205/6018; A61M 2205/6054; A61M 2205/6063; A61M 2205/6072; G06F 19/3406; G06F 19/3418  
USPC .............. 604/890.1, 500, 502, 503, 504, 506, 604/65–67  
See application file for complete search history.

(56) References Cited

U.S. PATENT DOCUMENTS 3,631,847 A   1/1972   Hobbs  
3,771,694 A   11/1973  Kaminski  
(Continued)

FOREIGN PATENT DOCUMENTS

WO   WO 2006/084464   8/2006  
WO   WO 2006/114297   11/2006  
(Continued)

OTHER PUBLICATIONS

International Search Report for PCT No. PCT/IL2009/000533.  
(Continued)

*Primary Examiner* — Andrew Gilbert  
(74) *Attorney, Agent, or Firm* — Dinsmore & Shohl LLP

(57) ABSTRACT

Disclosed is a dispensing system. The dispensing system includes a dispensing unit to dispense therapeutic fluid, and a validation mechanism to enable operation of the dispensing unit based, at least in part, on a determination of whether operation of the dispensing device is authorized.

19 Claims, 11 Drawing Sheets

(51) Int. Cl.
*A61B 5/145* (2006.01)
*A61M 5/172* (2006.01)
*A61M 5/145* (2006.01)
*G06F 19/00* (2011.01)

(56) References Cited

U.S. PATENT DOCUMENTS

| | | | |
|---|---|---|---|
| 4,498,843 A | 2/1985 | Schneider et al. | |
| 4,544,369 A | 10/1985 | Skakoon et al. | |
| 4,657,486 A | 4/1987 | Stempfle et al. | |
| 4,715,786 A | 12/1987 | Wolff et al. | |
| 5,957,895 A | 9/1999 | Sage et al. | |
| 6,485,461 B1 | 11/2002 | Mason et al. | |
| 6,589,229 B1 | 7/2003 | Connelly et al. | |
| 6,723,072 B2 | 4/2004 | Flaherty et al. | |
| 6,740,059 B2 * | 5/2004 | Flaherty | 604/67 |
| 6,749,587 B2 * | 6/2004 | Flaherty | 604/151 |
| 7,999,679 B2 * | 8/2011 | Van Alstyne | 340/572.1 |
| 8,274,389 B2 * | 9/2012 | Teeter | 340/572.3 |
| 8,444,607 B2 * | 5/2013 | Mounce et al. | 604/218 |
| 2005/0154368 A1 * | 7/2005 | Lim et al. | 604/403 |
| 2006/0290471 A1 * | 12/2006 | Van Alstyne | 340/10.1 |
| 2007/0124002 A1 * | 5/2007 | Estes et al. | 700/20 |
| 2007/0186923 A1 * | 8/2007 | Poutiatine et al. | 128/200.14 |
| 2007/0191690 A1 * | 8/2007 | Hasse et al. | 600/300 |
| 2007/0191702 A1 | 8/2007 | Yodfat et al. | |
| 2007/0270744 A1 * | 11/2007 | Dacquay et al. | 604/114 |
| 2008/0045930 A1 * | 2/2008 | Makin et al. | 604/890.1 |
| 2008/0077081 A1 * | 3/2008 | Mounce et al. | 604/67 |
| 2008/0214916 A1 | 9/2008 | Yodfat et al. | |
| 2008/0319414 A1 | 12/2008 | Yodfat et al. | |
| 2008/0319416 A1 | 12/2008 | Yodfat et al. | |
| 2010/0105735 A1 * | 4/2010 | Palmer et al. | 514/326 |
| 2010/0106083 A1 * | 4/2010 | Dacquay et al. | 604/67 |
| 2012/0209239 A1 * | 8/2012 | Gray | 604/500 |

FOREIGN PATENT DOCUMENTS

| | | |
|---|---|---|
| WO | WO 2007/052277 | 5/2007 |
| WO | WO 2007/092637 | 8/2007 |
| WO | WO 2007/104755 | 9/2007 |
| WO | WO 2008/024814 | 2/2008 |
| WO | WO 2008/078318 | 7/2008 |
| WO | WO 2009/066288 | 5/2009 |
| WO | WO 2009/125398 | 10/2009 |

OTHER PUBLICATIONS

Written Opinion of the International Search Authority for PCT No. PCT/IL2009/000533.

* cited by examiner

DEVICE, A SYSTEM AND A METHOD FOR IDENTIFICATION/AUTHENTICATION OF PARTS OF A MEDICAL DEVICE

CROSS REFERENCE TO RELATED APPLICATIONS

The present application is a 35 U.S.C. §371 national stage entry of PCT/IL2009/000533, which has an international filing date of May 27, 2009 and claims benefit to U.S. provisional patent application No. 61/057,088, filed on May 29, 2008, the entire disclosures of which are incorporated herein by reference in their entirety.

FIELD

The present disclosure relates generally to a system, a method and a device for sustained infusion of fluids. More particularly, the present disclosure relates to a portable infusion device comprising at least two parts and a method for the parts identification/authentication before and/or during the device is assembled from the parts. More particularly, the present disclosure relates to a skin securable dispensing patch comprising a reusable part, a disposable part and a cradle unit, and to a method for parts authentication/identification.

BACKGROUND

Diabetes mellitus is a disease of major global importance, increasing in frequency at almost epidemic rates, such that the worldwide prevalence in 2006 is 170 million people and predicted to at least double over the next 10-15 years. Diabetes is characterized by a chronically raised blood glucose concentration (hyperglycemia), due to a relative or absolute lack of the pancreatic hormone, insulin.

Treatment of diabetes mellitus requires frequent insulin administration that can be done by multiple daily injections (MDI) with syringe or by continuous subcutaneous insulin injection (CSII) with insulin pumps. In recent years, ambulatory portable insulin infusion pumps have emerged as a superior alternative to multiple daily injections of insulin. These pumps, which deliver insulin at a continuous basal rate as well as in bolus volumes, were developed to liberate patients from repeated self-administered injections, and allow greater flexibility in dose administration.

Several ambulatory insulin infusion devices are currently available on the market. Examples of first generation disposable syringe-type reservoir and tubes were disclosed in U.S. Pat. No. 3,631,847 to Hobbs, U.S. Pat. No. 3,771,694 to Kaminski, U.S. Pat. No. 4,657,486 to Stempfle, and U.S. Pat. No. 4,544,369 to Skakoon. Other dispensing mechanisms have also been discussed, including peristaltic positive displacement pumps, in U.S. Pat. No. 4,498,843 to Schneider and U.S. Pat. No. 4,715,786 to Wolff, the contents of all of which are hereby incorporated by reference in their entireties.

Although these devices represent an improvement over multiple daily injections, they nevertheless all suffer from several drawbacks, including, for example, their large size and weight, caused by their configuration and the relatively large size of the driving mechanisms and of the syringes. These relatively bulky devices have to be carried in a patient's pocket or be attached to the belt. Consequently, the fluid delivery tubes of the infusion set are very long, usually longer than 60 cm, in order to permit needle insertion at remote sites of the body. These uncomfortable bulky devices and long infusion set are rejected by the majority of diabetic insulin users since they disturb regular activities such as sleeping and swimming. Furthermore, the effect of the image projected on the teenagers' body is unacceptable. In addition, the delivery tube excludes some optional remote insertion sites, like buttocks, arms and legs.

To avoid the consequences of long infusion sets, a new concept, referred to as a second generation pump, was proposed. This concept includes a remote controlled skin adherable device with a housing having a bottom surface adapted to contact patient's skin, a reservoir disposed within the housing, and an injection needle adapted to communicate with the reservoir. These skin adherable devices are disposed every 2-3 days similarly to available pump infusion sets. These devices were described, for example, in at least in U.S. Pat. No. 5,957,895 to Sage, U.S. Pat. No. 6,589,229 to Connelly, and U.S. Pat. No. 6,740,059 to Flaherty. Additional configurations of skin adherable pumps were described, for example, in U.S. Pat. No. 6,723,072 to Flaherty and U.S. Pat. No. 6,485,461 to Mason, the contents of all of which are hereby incorporated by reference in their entireties. These devices also have several limitations: they are also bulky and expensive. Their high selling price is due to the high production and accessory costs; the user must discard the entire device every 2-3 days, including the relatively expensive components, such as driving mechanism and electronics.

A third generation dispensing device, such as the Medingo device described in co-pending/co-owned U.S. publication no. 2007-0106218 and International Patent Application No. PCT/IL06/001276, the contents of all of which are hereby incorporated by reference in their entireties, is a miniature portable programmable fluid dispenser that has no tubing and can be attached to the patient skin. It includes of two parts, a disposable part (DP) and a reusable part (RP). After connection of the reusable and the disposable parts, the unified dispensing unit presents a thin profile. The RP contains electronics and other relatively expensive components and the DP contains reservoir. The Medingo device includes a remote control unit that enables data acquisition, programming, and user inputs. An improvement to a skin adherable pump that includes of the two parts is described in co-pending/co-owned U.S. publication no. 2008-0215035 and International Patent Application No. PCT/IL09/000,388, the contents of all of which are hereby incorporated by reference in their entireties. In this application, a device, a system and a method for connection and disconnection of a skin securable pump is disclosed. The system enables the use of a cradle, which is initially adhered to the skin and then a cannula is inserted through the cradle into the body of the user. The cannula, which is a sterilized component, is provided to the patient protected in a cannula cartridge unit. An example for such cannula cartridge unit including a cannula is described in co-pending/co-owned U.S. publication 2008-0319416, the content of which is hereby incorporated by reference. The two-part pump can be consequently connected and disconnected to and from the cradle upon patient discretion. The cannula, cradle, and disposable part are all designed for a single use and are preferably sterilized, to prevent contaminations, irritations, infections and other ill effects. And thus, they should be replaced every several days (e.g. once or twice a week).

Such a device, as described in the above-mentioned patents assigned to Medingo, comprises a number of parts, some of which are disposable. These parts require authentication and identification before and/or during assembling the parts for the following reasons:
1. Intentional or inadvertent reuse of any of the parts might have hazardous consequences on the user. For example, reuse of a cannula may lead to a local, and even systemic infection, reuse of a reservoir may lead to a deficiency of insulin which might result in hyperglycemia. Identification and authentication would allow tracking of the different parts and thus prevent their intentional or inadvertent reuse. Tracking can be done for example, by storing the serial number of the assembled disposable parts in the memory and preventing assembling from disposable parts with the same serial number.

2. As part of the quality control of the genuine device, inspections and tests are carried out, and all components and materials must conform to pre-defined specifications. Use of imitations instead of genuine parts might have hazardous consequences on the user because the imitations do not undergo strict quality control and therefore do not conform to the high standards that the genuine parts must meet. For example, use of imitation parts that do not meet the sterility standards may lead to infections. Authentication of the different parts during assembly of the parts may therefore prevent the use of imitations.

3. Use of parts whose expiry date has elapsed might have hazardous consequences on the user, for example, the consequence of using insulin after expiry date is deleterious. Determination of the expiry date of the different parts during their assembly may thus prevent the use of parts whose expiry date has passed.

4. Assembling of device from parts belonging to different users might also have hazardous consequences on the user. For example, the DPs of different users may comprise different reservoir volumes or different therapeutic agents (e.g. insulin 100 U/mL or 40 U/mL), and faulty assembly may therefore result in fatal consequence due to underdosing or overdosing. Parts identification may prevent assembling of device from RPs and DPs belonging to different users.

Parts identification and/or validation could therefore prevent intentional or inadvertent reuse of any of the parts.

SUMMARY

Some embodiments of the present disclosure describe a portable device comprising multiple parts, from which the device is assembled. The device, upon assembly, delivers therapeutic fluid (e.g., insulin) into the body and implements a method for identification and authentication (i.e. validation) of the different parts of the device before and/or during device assembly.

In some embodiments the device comprises, a processor, controlling the driving mechanism according to at least some of the data received from a user, an identification means (e.g. ID marker) for authenticating a portion (e.g. part, component) of the system, an identification reading means (e.g. ID reader) for reading the identification means and for providing a signal to the processor.

According to some embodiments the device further comprises a cradle unit configured to secure a dispensing unit onto the body of the user, includes the ID marker, which provides indication to an ID reader.

In some embodiments the identification means is associated with a cannula. The cannula is insertable into the body of the user, providing a fluid path between a reservoir containing the therapeutic fluid and the user's body.

In some embodiments the identification means is associated with a reservoir. The reservoir is configured to contain a therapeutic fluid.

In some embodiments the identification reading means is located in a dispensing unit. According to some embodiments the dispensing of the therapeutic fluid may be enabled and/or disabled based on the validation of the identification means.

In some embodiments the identification reading means is located in a remote control unit. The remote control unit may communicate with the patch unit and may be enable its programming, user input, and/or data acquisition.

In some embodiments the identification reading means is located in an inserter, configured to insert a cannula into the body of a user. According to some embodiments the insertion of the cannula can be enabled and/or disabled based on the validation of the identification means.

The system according to some embodiments of the present disclosure comprises a dispensing patch unit (also referred-to as a "patch unit" and/or "dispensing unit") and, in some embodiments, may be part of a system which includes a remote control unit, a cradle unit and a cannula cartridge unit.

Some embodiments of the present disclosure describe a system comprising multiple parts. The system is configured to enable the programming of therapeutic fluid (e.g., insulin) delivery into the body and to deliver the therapeutic fluid. The system implements a method for identification and authentication (i.e. validation) of the different parts of the system.

In some embodiments the system comprises a reservoir to contain a therapeutic fluid (e.g. insulin), a cannula insertable into a body of a user, enabling fluid communication between the reservoir and the user's body, a driving mechanism including a motor and at least one gear, configured to engage with the reservoir to dispense the therapeutic fluid, a user interface configured to receive data from the user and to notify the user, at least one processor, controlling the driving mechanism according to at least some of the data received from the user, an identification means (e.g. ID marker) for authenticating at least a portion of the system, an identification reading means (e.g. ID reader) for reading the identification means and for providing a signal to the at least one processor and at least one power source (e.g. battery) to provide power to at least one of the driving mechanism, the identification means, the at least one processor and the user interface.

According to some embodiments, the processor can change the status of the system to enable/disable at least one function of the system based on the signal received from the identification reading means.

In some embodiments the identification means comprises an identification tag storing the identification information, and the identification reading means comprises an identification reader to read the identification information stored on the identification tag.

In some embodiments the identification means includes an RFID transponder and the identification reading means comprises an RFID antenna.

In some embodiments the identification means includes a digital memory storing the identification information and the identification reading means comprises a digital memory reader.

In some embodiments the identification means includes a bar code representative of the identification information, and the identification reading means comprises a bar code reader.

In some embodiments, authentication includes establishing or confirming a product or a part is genuine.

The system according to some embodiments of the present disclosure comprises a dispensing patch unit and, in some embodiments, may be part of a system which includes a remote control unit, a cradle unit and a cannula cartridge unit. The remote control unit may communicate with the patch unit and may enable its programming, user input, and/or data acquisition. The cradle unit according to some embodiments may be configured as a substantially flat plate that adheres to the skin and enables patch disconnection and reconnection upon patient discretion. Some embodiments of the cannula cartridge unit include a cannula that is insertable through a passageway in the cradle unit. In some embodiments, the system further comprises an inserter to insert the cannula into a body of a user.

Identification and authentication can be possible for one or more parts of the system. In some embodiments, the patch unit is composed of two parts—a disposable part which will be referred-to as DP and a reusable part which will be referred-to as RP. Parts authentication may be achieved by providing an identification marker (e.g. RFID identification tag) at the DP and an identification reader at the RP.

In some embodiments, an identification tag can be deployed in and/or on the cradle unit and an identification reader provided for with the patch unit allowing identification and authentication during the patch disconnection and reconnection, for example. That is, the patch unit may identify the cradle unit each time they are reconnected, and thus, for example, reconnection of patch units belonging to different users is prevented. Furthermore, in some embodiments, delivering therapeutic fluid (e.g. insulin) into a body of a patient may depend on the identification and/or authentication during patch disconnection and reconnection. For example, therapeutic fluid delivery may be suspended when there is no identification reading and resumed when there is an identification reading. Additionally and/or alternatively, the operation of the patch unit may be altered based on the identification reading to enable usage in emergency situations even if there is no authentication and/or there is a mismatch of the identification reading (e.g. using parts form different users).

A therapeutic fluid dispensing system according to some embodiments of the present disclosure comprises a patch (i.e., dispensing) unit and a remote control unit. The remote control unit may communicate with the patch unit and/or enable programming, user input, and/or data acquisition of the patch unit. Communication between the units (e.g. remote control unit and patch unit) may be identified by at least one specific key shared by the units (for example). Setting the key shared by the units may also be referred to as "pairing". Paired units communicate with each other, but do not communicate with other units. Pairing the units and/or transferring the shared key can be done, for example, by reading an identification means (e.g. identification tag).

Accordingly, an object of some of the embodiments of the present disclosure is to provide a dispensing device (and in some embodiments, a system) that comprises more than one part and implements a method for identification and authentication the different parts of the device/system before and/or during the assembling of the parts.

Another object of some of the embodiments of the present disclosure is to provide a dispensing device (and in some embodiments, a system), which comprises one or more reusable parts having an identification reader and one or more disposable parts having an identification tag, and which is configured to perform identification and authentication (whichever the case may be) of the reusable and disposable parts.

Another object of some of the embodiments of the present disclosure is to provide a dispensing device, for example, which comprises one or more reusable parts having an identification FLASH reader and one or more disposable parts having a FLASH identification tag, and which is configured to perform parts identification and authentication employing a Read Write memory FLASH system.

Another object of some of the embodiments of the present disclosure is to provide a mechanical identification marker and a mechanical reader. The mechanicals reader and identifier interact with each other to enable mechanical connection. In some embodiments the identification marker fits to the identification reader as a key to a lock. Additionally and/or alternatively the connection between the identification marker and the identification enable at least one function of the system, preferably the dispensing of therapeutic fluid to the body of a user.

Another object of some of the embodiments of the present disclosure is to provide a method to identify, authenticate and/or validate components of system for dispensing a therapeutic fluid to a body of a user. The method may include reading an identification means with the identification means reader and disabling/enabling at least one function of the system according to the signal provided from the identification means reader.

Some embodiments of the present disclosure describe a system comprising multiple parts. The system is configured to enable the programming of therapeutic fluid (e.g. insulin) delivery into the body and to deliver the therapeutic fluid. The system implements a method for identification and authentication (i.e. validation) of the different parts of the system.

Yet another object of some of the embodiments of the present disclosure is to provide a dispensing device, for example, which comprises one or more reusable parts having an identification antenna, serving as an identification reader and one or more disposable parts having a transponder, serving as an identification tag, and which is configured to perform parts identification and authentication employing a Radio Frequency Identification Devices (RFID).

A further object of some of the embodiments of the present disclosure is to provide a dispensing device, for example, which comprises one or more reusable parts having barcode scanner serving as an identification reader and one or more disposable parts having barcode serving as an identification tag, and is configured to perform parts identification and authentication employing a barcode system.

Yet another object of some of the embodiments of the present disclosure is to provide a dispensing device which comprises one or more reusable parts having a miniature mechanical lock as an identification reader and one or more disposable parts having a miniature mechanical key as an identification tag, and which is configured to perform parts identification and authentication employing a miniature mechanical key-lock system.

It would therefore be desirable to implement parts authentication to avoid imitations and to make sure that genuine parts are used.

It would also be desirable to implement parts identification to verify that parts expiry date has not lapsed.

Parts identification would also be desirable to prevent assembly of RPs and DPs of different users.

Accordingly, it would be desirable to provide a third generation dispensing device and a method for identification and authentication of the different parts, from which it is assembled before and/or during assembling.

It would also be desirable to provide a device that delivers insulin into the body and can concomitantly continuously monitor glucose in the body (e.g. contained in blood, ISF) and perform identification and authentication of the different parts of the device during device assembly.

It would further be desirable to provide a device which is miniature, discreet, economical for the users and cost effective, as well as to provide a method for identification and authentication of the different parts of the device during device assembly.

It would additionally be desirable to provide a device that includes a miniature dispensing patch unit that can be connected and disconnected to and from a skin adhered cradle unit upon patient discretion and can continuously/periodically dispense insulin and implement a method for identification and authentication of the different parts of the device during device assembly.

It would also be desirable to provide a device that comprises an insulin dispensing patch unit that can be remotely controlled and could perform identification and authentication of the different parts of the device during device assembly.

It would further be desirable to provide a device that comprises a remote control unit than communicates with insulin dispensing patch unit, and could perform identification and authentication of the different parts of the device during device assembly.

It would also be desirable to provide a device that comprises a miniature skin securable dispensing patch that can continuously dispense insulin and monitor body glucose concentration levels, and could perform identification and authentication of the different parts of the device during device assembly.

BRIEF DESCRIPTION OF THE DRAWINGS

FIG. 4b is a perspective view of the exemplary system of FIG. 4a.

DETAILED DESCRIPTION

Embodiments disclosed herein are directed to insulin dispensing devices and systems, which may include a dispensing unit to dispense insulin, and a validation (i.e. authentication) mechanism to enable operation of the dispensing unit based, at least in part, on a determination of whether operation of the dispensing, device is authorized. In some embodiments, the validation mechanism comprises an identifier coupled to the first module of the dispensing unit to indicate identification information associated with the first module, and an identification receiver coupled to the second module of the dispensing unit to receive the identification information associated with the first module.

Figure 1A:
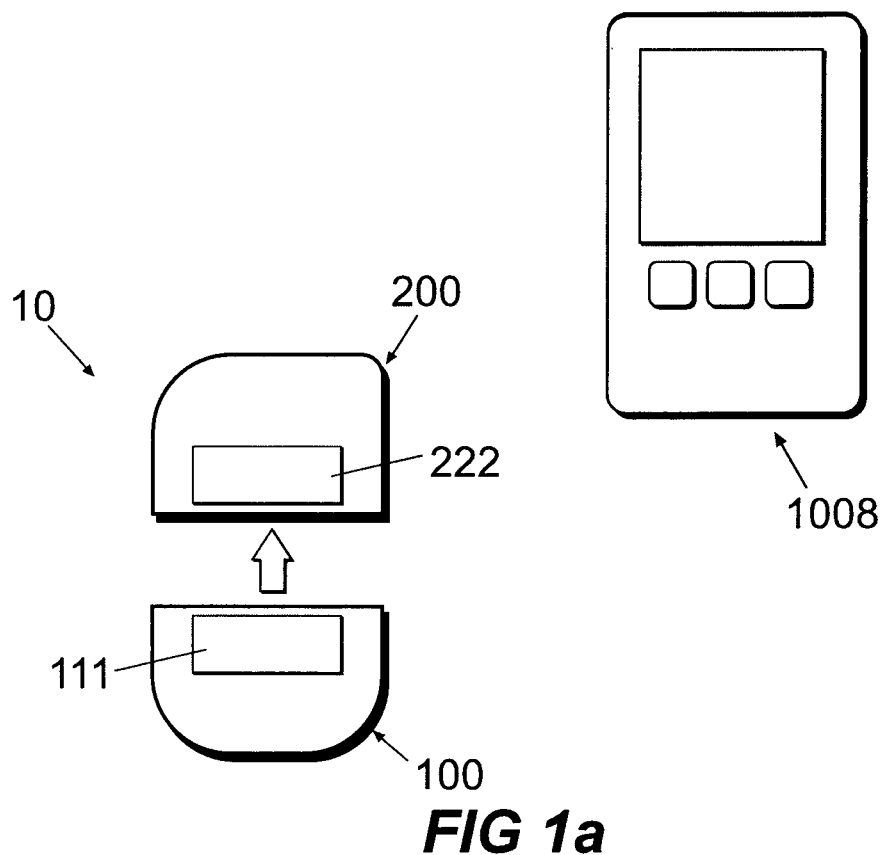
FIGS. 1a-b are schematic diagrams of an exemplary dispensing device comprising a two-part patch unit, as well as a remote control unit, according to some embodiments of the present disclosure.
Figure 1B:
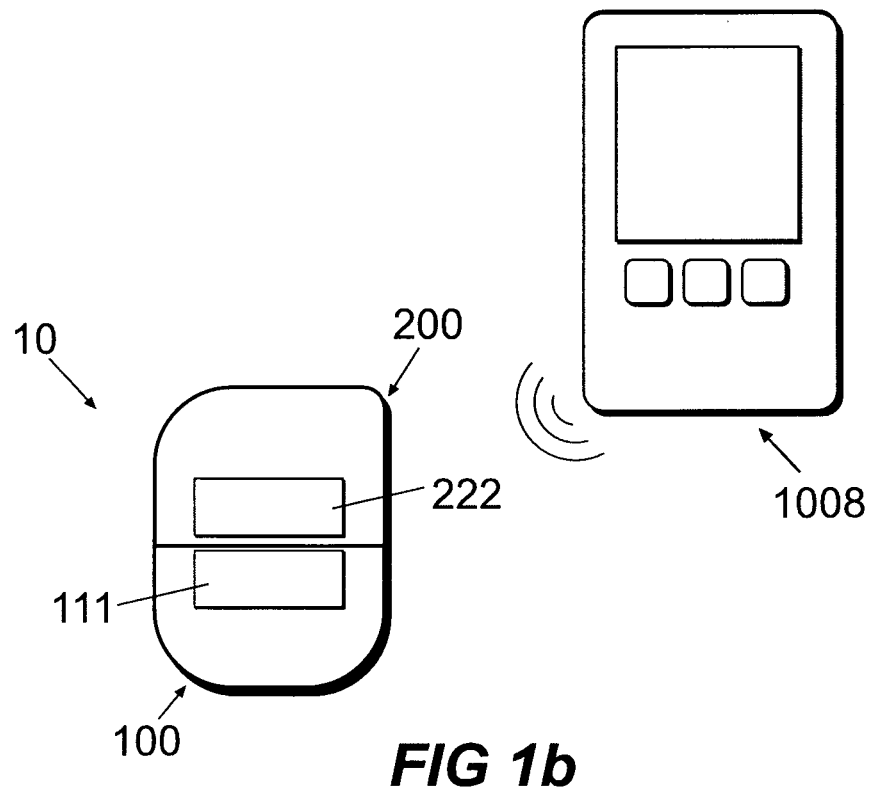

FIGS. 1a-b are schematic diagrams of a dispensing system that includes a remote control unit 1008 and a dispensing patch unit 10. FIG. 1a depicts a two part dispensing patch unit 10 comprising a disposable part (DP) 200 and a reusable part (RP) 100. FIG. 1b depicts dispensing patch unit 10 assembled from DP 100 and RP 200 attached together In some embodiments, the DP comprises an identification marker (e.g. RFID tag), 222, and the RP comprises an identification reader 111. Operation of dispensing unit is authorized, for example, if the identification reader 111 identifies the identification tag 222.

Figure 2:
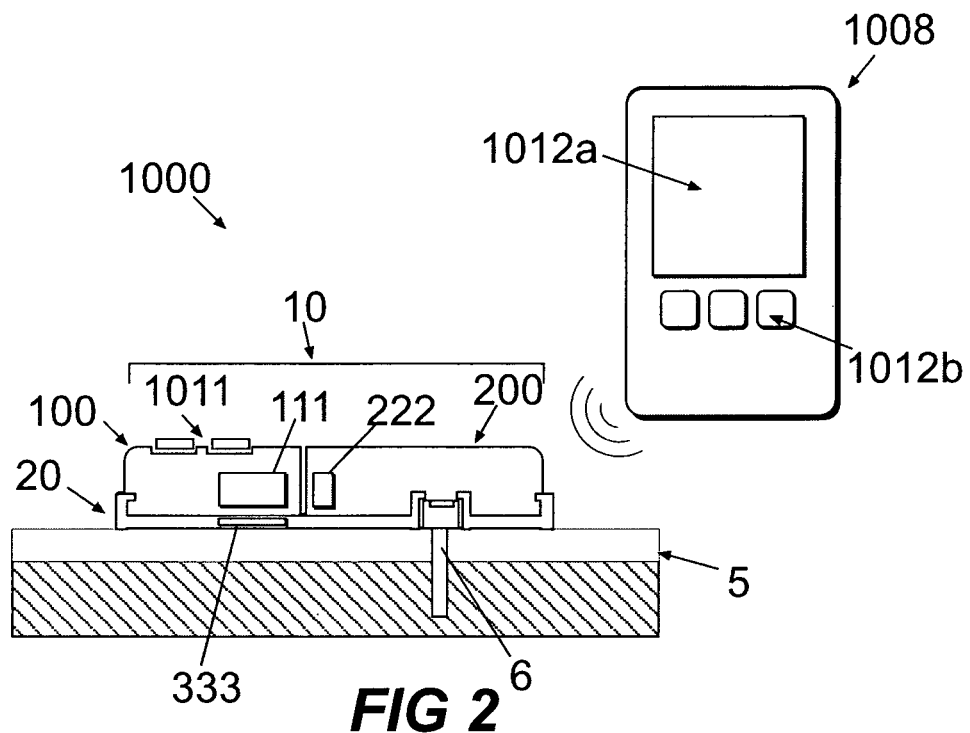
FIG. 2 is a schematic diagram of an exemplary infusion device that comprises a two-part patch unit secured to a skin-adherable cradle unit, as well as a remote control unit, according to some embodiments of the present disclosure.

Referring to FIG. 2, an exemplary embodiment of a system 1000 for dispensing therapeutic fluid (e.g. insulin) into a body of a patient (which is typically the user of the system). The system includes an infusion device configured as a two-part patch unit 10. The patch unit 10 is securable to a skin adherable cradle unit 20. The system also comprises a remote control unit 1008 which communicates with the dispensing patch unit 10, enabling programming, user inputs and data acquisition. In some embodiments, the remote control unit may comprise a PDA, watch, laptop, PC, iPod, iPhone or any other remote controlled device.

In some embodiments, the fluid delivery device/system can further comprise a sensing apparatus to monitor bodily analyte(s) e.g., monitoring of concentration levels of glucose in the interstitial fluid ("ISF"). The sensing apparatus may comprise sensors, probes, electrodes, sensing elements, dedicated processing elements, delivery modules and components, etc. Sensing of the analyte(s) can be performed within the body ("in vivo") or outside the body, and may be performed by various techniques such as optical techniques, electrochemical techniques, etc. The sensing apparatus can measure analyte concentration at measurement rates (or frequencies) that are either continuous, semi-continuous, periodic or discrete. Such a sensing apparatus is described in detail in co-pending/co-owned U.S. patent application Ser. No. 11/706,606 and 11/963,481, and in co-pending/co-owned International Patent Application No. PCT/IL2008/001521, the contents of which are hereby incorporated by reference in their entireties. Components of the sensing apparatus can further include identification readers and markers.

In some embodiments, a dispensing apparatus and sensing apparatus (constituting a "system") is configured to operate in one or more of a closed loop, an open loop, or a semi-open loop mode.

The system 1000 may comprise a removable cannula 6 to penetrate the user's skin 5. The patch unit 10 may be attached to a cradle unit 20 that may be structured, for example, as substantially flat sheet (or plate) adherable to the user's skin 5. The use of the cradle unit enables connection/disconnection of the patch unit 10 to and from the body. Embodiments of such system are described for example in a co-pending/co-owned U.S. publication no. 2007-0106218 and 2008-0215035, the disclosures of which are herein incorporated by reference in their entireties.

An insertion device (also referred to as "inserter") can be applied for inserting the cannula 6 into the user's body. An example for such insertion device is described in a co-pending/co-owned U.S. publication no. 2008-0319414, the contents of which is hereby incorporated by reference.

Manual inputs can be provided by one or more buttons 1011 located at the dispensing patch unit 10. The components of the dispensing patch unit 10 can be accommodated in one housing or in two housings or more. If the components are accommodated in two housings, one of the housings can generally host complex/expensive components in the reusable part (RP) 100 and the other housing can host simpler/inexpensive components in the disposable part (DP) 200.

In accordance with some embodiments, the DP includes an identification tag (also referred to as "ID tag") 222, and the RP includes an identification reader (also referred to as "ID reader") 111. Furthermore, in some embodiments, a remote control unit for the dispensing device may include an identification reader.

In some embodiments, the functions carried out by the patch unit may be based on information received from the identification tag 222 via the identification reader. For example, the received information may be processed to authenticate (e.g. validate) the disposable part. The processing may include, for example, demodulating the received information and comparing at least some of the demodulated information with other data stored in the dispensing system. Thus, for example, the information received from the identification tag can comprise one or more of an expiration date, a batch number, a serial number, a manufacturer, therapeutic fluid compatibility (e.g. whether it is compatible with a specific brand of therapeutic fluid/insulin), a lifetime period, a volume of the part, and the like.

Accordingly, pursuant to some embodiments, based on the identification reading and processing the dispensing unit 10 may change its functionality. For example, when the expiration date of the part has past, the therapeutic fluid delivery will be limited, or completely stopped.

In some embodiments, the cradle unit 20 can comprise its own identification tag 333. For example, after connection of the assembled two parts of the patch unit with cradle unit, the patch unit's status can change and/or enable the delivery of therapeutic fluid, when the information stored on the identification tag 333 is read and identified by the identification reader 111 of the RP and subsequently authorized.

Identifying the identification tag 333 can be done periodically and/or as part of other procedures (e.g. before therapeutic fluid delivery, upon connection of the patch unit to the cradle unit). Thus, the status of the patch unit 10 can be changed when there is no identification and/or authorization, in case that the patch unit 10 is disconnected from the cradle unit 20, e.g. pausing the delivery of therapeutic fluid.

In some embodiments, the cradle unit 20 and the DP 200 may comprise identification tags, 333 and 222 respectively, and the RP 100 may comprise an identification reader 111 to identify and authorizes both ID tags 333 and 222.

In some embodiments, the insertion device includes an identification reader. According to these embodiments, the insertion of a cannula is enabled when the identification tag is authenticated by the identification reader located in the insertion device. Additionally/alternatively the identification tag can be located on the cannula cartridge. In further embodiments, the cannula may be a part of a cannula cartridge unit (which can also include a penetrating member, cannula hub and a septum), and/or an infusion set.

In some embodiments the remote control unit 1008 includes an identification reader. Additionally, the remote control unit 1008 may communicate with RP 100, according to the identification reading. For example, the remote control unit 1008 can transfer the identification reading to RP 100. Alternatively, the remote control unit may transfer the authentication and/or the identification status (e.g. if the reading are within acceptable range).

In some embodiments pairing the remote control unit to the RP and/or transferring the key required for the pairing procedure, can be done by reading an identification tag.

Figure 3:
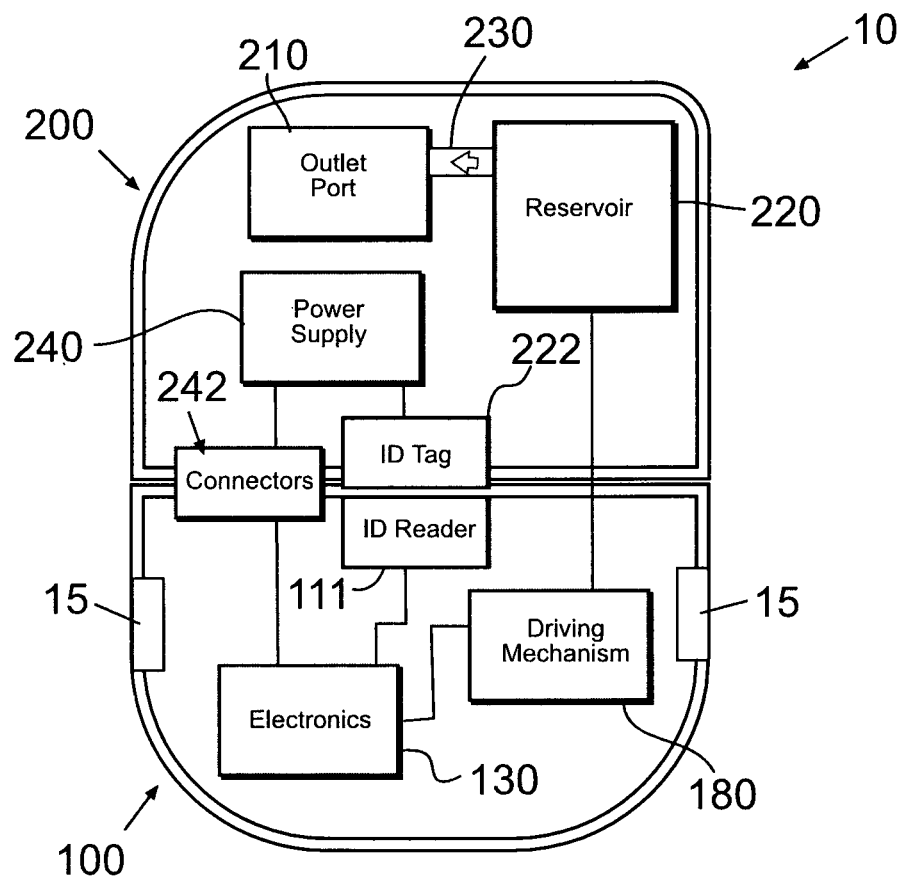
FIG. 3 is a schematic diagram of an exemplary two parts of the patch unit including two apposing identification components according to some embodiments of the present disclosure.

FIG. 3 shows schematically various components of the dispensing patch unit 10 that are disposed within the reusable part 100 and the disposable part 200 according to some embodiments.

In some embodiments, the disposable part 200 may include an identification tag 222, as well as a power supply 240, a reservoir 220, delivery tube 230, and outlet port 210. The reusable part 100 may include an identification reader 111, as well as electronics 130, at least a portion of a driving mechanism 180, and operation buttons/switches 15. According to such embodiments, power for activating the identification reader 111 located in the RP may be provided from power supply (e.g. battery) 240 located in the DP. Electrical connection between the two parts (RP and DP) can be established for example by a connector 242, which are shared between the two parts. Thus, reading an identification means (e.g. identification tag 222) can be enabled when the dispensing patch unit 10 is assembled. In some such embodiments, it is preferred to read the identification tag of a new DP, before replacing the older disposable part 200, while it is still connected to the reusable part 100. Alternative embodiments may include an additional power supply (which may be located in the RP for example) electrically connected to the identification reader 111, enabling identification when no disposable part 200 is connected.

The patient can operate the dispensing unit 10 either by a remote control unit 1008 (as shown in FIG. 2) or by one or more buttons/switches 15 located on the dispensing unit 10. In some embodiments, operation based on the buttons 15 may be directed for bolus dose delivery.

In some embodiments, the driving mechanism can be constituted by components disposed in both parts (DP and RP). In some embodiments, the power supply may be included in the reusable part, or shared between both parts (DP and RP).

Because the ID reader is generally more expensive than the ID tag, and because the RP will generally house the relatively expensive components of the patch unit, in some embodiments, the identification tag 222 may be located in the DP while the identification reader 111 may be located at the RP. However, alternatively, the ID tag may be located at the RP and the identification reader may be located at the DP.

Figure 4A:
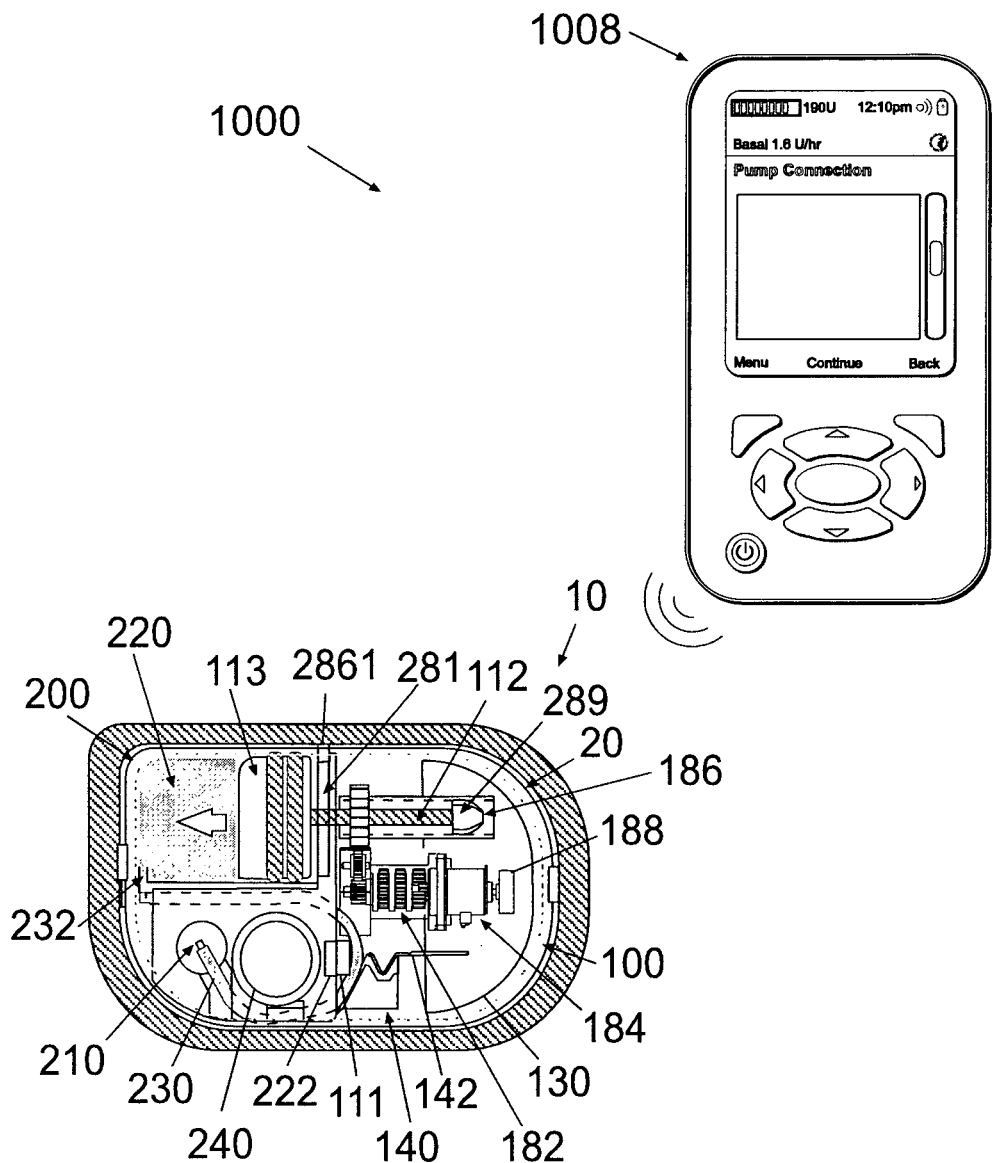
FIG. 4a is a schematic diagram of an exemplary system for dispensing a therapeutic fluid to a patient according to some embodiments of the present disclosure.

FIG. 4a shows an exemplary embodiment of a fluid dispensing device/system 1000 for dispensing a therapeutic fluid to a patient. The system 1000 includes a fluid dispensing patch unit 10, a remote control unit 1008, and a cradle unit 20. The dispensing patch unit 10 includes a reusable part 100 and a disposable part 200. The reusable part 100 is configured to be detachably connected to the disposable part 200. The system functionality (e.g. status, mode of operation), may be based at least in part on identification and authentication of the assembled parts comprising the dispensing patch unit. The functions that may be affected according to the identification and/or authentication typically includes dispensing therapeutic fluids, programming the system (e.g. setting the amount of fluid to be delivered), activation of the dispensing unit (i.e. making it operable) and/or deactivation of the dispensing unit. The identification and/or authentication may be performed upon the attachment of the two parts via an ID tag 222 located at the disposable part and via an ID reader 111 located at the reusable part. The assembled patch unit may be connected and disconnected from the cradle unit 20 upon user discretion and, in some embodiments, the assembled patch unit functionality (e.g. pause/suspend/resume the dispensing of the therapeutic fluid) may be changed according to the ID reading. The ID reading performed by the ID reader (e.g. ID reader 111 located at the reusable part 100), can generate a signal (or a set of signals) based on the ID tags being read (e.g. ID tag 333 located at the cradle unit 20).

In some embodiments, the assembled patch unit functions are determined based on the identification and/or authentication of an ID tag. It is preferred in such embodiments, to enable wireless communication (e.g. RF communication, IR communication) and programming of the assembled patch unit, regardless of the ID tag reading, while the dispensing of a therapeutic fluid to a patient is based upon the ID tag reading. For example, the assembled patch unit can dispense bolus amounts of therapeutic fluid after ID tag reading, while full functionality of the assembled patch unit (e.g. bolus and basal delivery) is enable after authentication of the ID tag. These modes of operation enable the usage of the device in emergencies, but prevent the full usage without authentication. Furthermore, some embodiments enable only manual bolus delivery (i.e. bolus programmed using buttons located on the patch unit), without an authentication.

FIG. 4a illustrates an exemplary disposable part 200 having a reservoir 220 and a piston 113 forcibly displaceable along the reservoir. The piston 113 is connected to a threaded piston rod 112 having a tip 289 with teeth. The piston rod 112 may be manually gripped at the tip 289 to enable manual linear displacement of the piston 113 along the reservoir 220. An engagement member 2861 may be provided, located within a chassis 281. By virtue of such an engagement member, the piston may be displaced along the reservoir according to one of the two modes: a first mode enabling free displacement of the piston rod, and a second mode enabling a controlled displacement of the piston rod.

The disposable part 200 includes an outlet port 210 having a connecting lumen (not shown in FIG. 4a). The connecting lumen is fluidly coupled to the reservoir 220 through a connecting tube 230 and fluid channel 232. The connecting tube 230 can be supported by and deployed on a chassis (indicated by dotted lines in FIG. 4a). The disposable part 200 further includes a power supply 240 (e.g. a battery) which supplies electrical energy to at least one of the reusable part 100 and/or the disposable part 200 when the two parts have been assembled (as illustrated in FIG. 4a).

The reusable part 100 includes at least a portion of a driving mechanism having a motor 184 and gears 182 to drive a threaded cylinder referred-to as a "sleeve" 186. In some embodiments, the motor 184 can comprise a Stepper motor, DC motor, SMA actuator or the like. The reusable part 100 can further comprise at least a portion of an occlusion sensor 140 with a sensor 142 which electrically connected to the PCB/electronics 130. The occlusion sensor 140 is configured to monitor the fluid condition in its delivery path, e.g. in the connecting tube 230 and/or connecting lumen and/or cannula. Such an occlusion may prevent delivery of therapeutic fluid to the patient's body. The occlusion sensor 140 may thus alert/notify the user (e.g. by displaying an alert on a screen (located on the dispensing unit 10 and/or on the remote control unit 1008, and/or any other notification mechanisms or modules, such as buzzer or vibrator) that a partial or complete occlusion has occurred and that it is time to replace the disposable part 200. Based on signals provided by the occlusion sensor 140, operation of the dispensing unit 10 may be halted/suspended.

The sleeve 186 is configured to receive the piston rod 112 of the disposable part 200 upon assembly/connection of the two parts (100 and 200), and to transfer rotational moment/force to the tip 289 and the piston rod 112. The reusable part 100 further includes electronics designated by the common numeral 130. The electronics may comprise a controller, a processor, a transceiver, an antenna etc.

In some embodiments, in which the power supply 240 is located in the disposable part 200, the reusable part 100 may include dedicated connectors to establish electrical communication between the power supply 240 (e.g. a battery) and electronics 130.

Figure 4B:
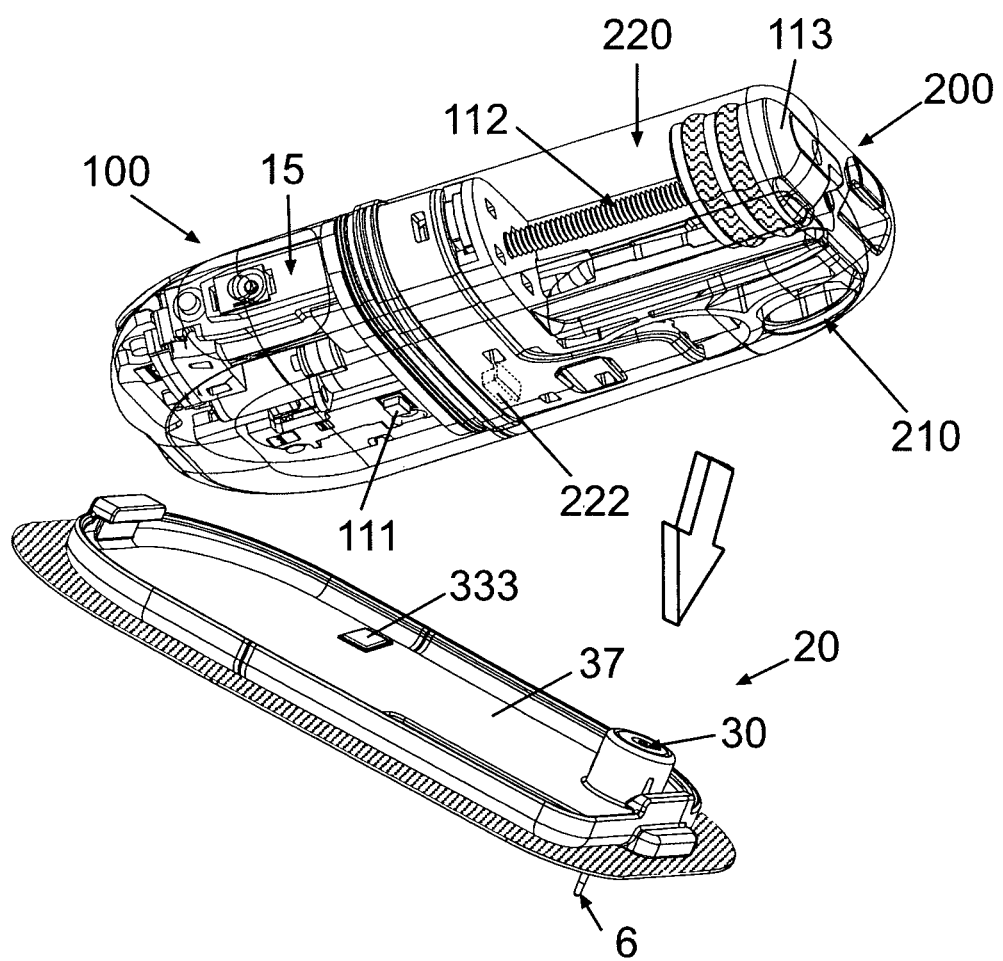

Referring to FIG. 4b, a perspective view of an exemplary embodiment of the connection of the dispensing patch unit 10 to the cradle unit 20 is shown.

An ID tag 333 located on the base 37 of the cradle unit 20, can be identified by an ID reader 111 located at the reusable part 100, and the assembled patch unit 10 becomes operable only upon identification and authentication which have been performed during/after patch unit 10 connection to the cradle unit 20. The cradle unit may also comprise a well 30 through which the cannula 6 can be inserted to the subcutaneous tissue.

The fluid dispensing device partially described above is disclosed in our co-owned/co-pending International Patent Application No. PCT/IL09/000,388, the content of which is hereby incorporated by reference in its entirety.

The above-mentioned identification tags 222, 333 located at the DP and at the cradle unit can be one or more of, for example, an RFID transponder, a barcode, and/or a FLASH memory, rewriteable memory and the like.

According to some embodiments, the identification information stored in the ID tags 222, 333 is received and/or read by the ID reader 111 provided at the RP. Subsequently, a determination is made whether the identification information corresponds to pre-defined data stored (e.g. in a memory), for example, on the RP part. The identification information is preferably sufficient to enable unequivocal identification and authentication of the parts. This information may include, for example, at least one of a manufacturing date and a batch number, such that upon completing the identification/authentication, imitation of DPs, and intentional or inadvertent use of DPs would be prevented.

Additional information such as amount, type and concentration of insulin in the reservoir of the DP, expiration date, patient personal information such as name, and prescription requirements may also be included in the information stored by the DP identification tag.

The ID reader may be located proximally to the ID tags when the RP and DP are connected and the patch unit is connected to the cradle unit.

Alternatively, the ID tags and ID reader can be located anywhere on the RP, DP, and cradle unit and wireless communication between the ID tags and ID reader may be implemented to enable identification of the ID tags by the ID reader located relatively remote from one another.

The identification reader 111, configured to read the information stored in the ID tag 222 located at the DP, may be, for example, an RFID antenna, a barcode scanner, and/or a FLASH memory reader.

In some embodiments, the process of identification and authentication of the parts may be mechanical instead of electrical. Under these circumstances, the validation mechanism would be such that it would be mechanically feasible or not feasible to connect the RP, the DP, and/or the cradle unit. Thus, operation of the dispensing device would be enabled if the parts can be mechanically connected to each other. For example, a "lock" and a "key" may be provided at the respective parts of the device and the device would operate, under these circumstance, if the key of one part mechanically fits (e.g., in a mating configuration) in the lock of another part of the device.

In some embodiments, the process of parts identification and/or authentication may be both electrical and mechanical. For example, if the information stored in the identification tag 222 is not identified and/or authenticated by the identification reader 111, then a physical configurational change may mechanically prevent parts assembly or device performance, thus rendering the device inoperable (i.e. unable to dispense therapeutic fluid). For example, one such physical configurational change may be the intentional occlusion of the tube through which insulin is dispensed.

In some embodiments, the data received by the ID reader is transferred to a processor-based device (not shown), included in the electronics 130, that can compare the information stored in the identification tag, and read by the identification reader, with a dedicated validation data stored within a database provided in a storage device (e.g. non volatile memory) which is in communication with the processor. For example, the validation data may include acceptable/pre-defined expiry dates according to manufactured batches. If a DP with an unacceptable expiry date is assembled, the expiry date will be compared with the acceptable expiry dates stored in the validation data and device operation will thus be restricted.

In such embodiments, the dispensing unit 10 would become operational after the identification reader 111 identifies the identification tag 222 and the information read by the reader 111 has been validated by the processor.

Figure 5:
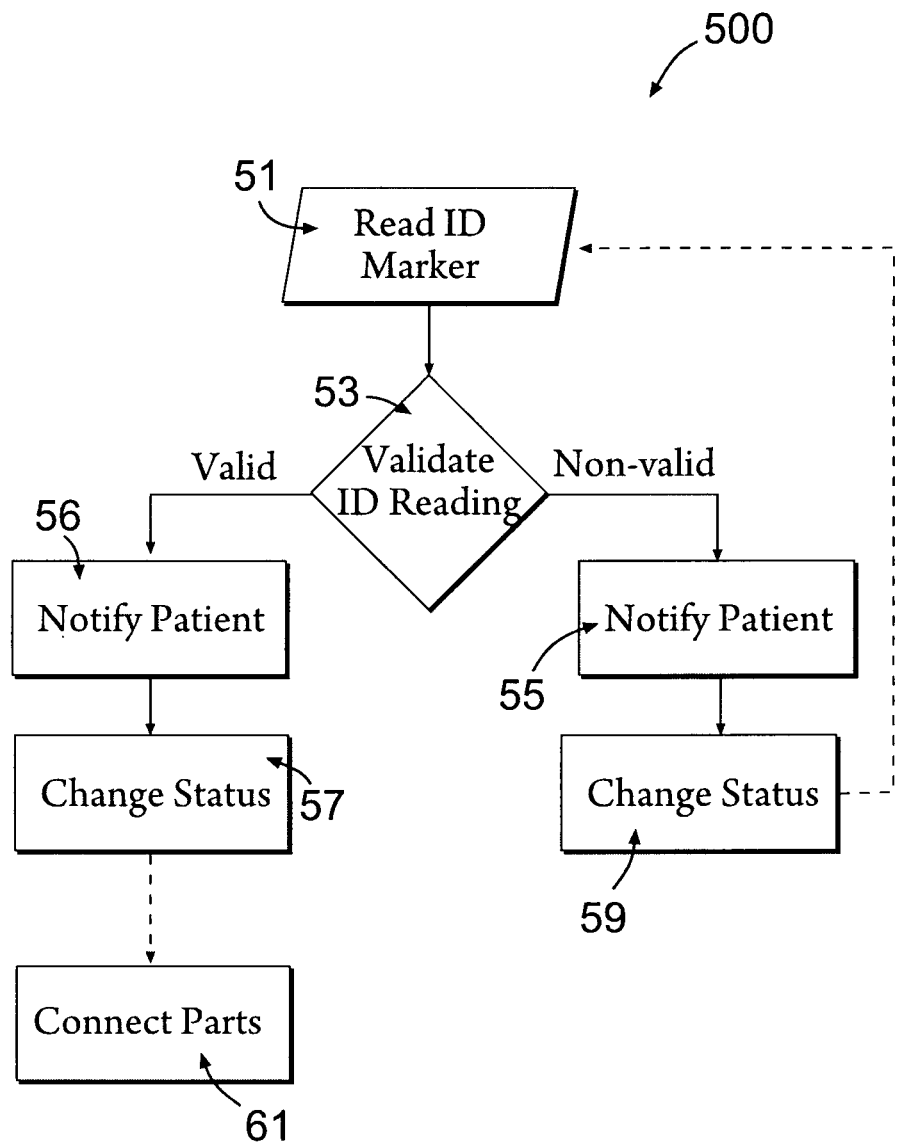
FIG. 5 is a flow chart of an exemplary procedure performed with respect to apposing the identification tag and identification reader according to some embodiments of the present disclosure.

In some embodiments, the validation data may be updated, as described in detail in FIG. 5. FIG. 5 shows a flow chart of an exemplary embodiment of identification procedure 500. The procedure is typically performed upon components (e.g. cannula, cradle, reservoir, etc.) replacement (e.g. when replacing a reservoir), periodically, and when other operation of the system/device are effected (e.g. verifying cradle identification before delivering therapeutic fluid). The information stored in the identification marker (e.g. ID Marker) is read by the identification reader, at step 51. The read information validity is evaluated, at step 53, preferably by processing it and comparing it to data stored in a validation database.

If the read data is valid, a notification is provided to the user, shown in step 56. The notification typically includes a conformation about the validation process and data related to the identification marker. The validation results in status change 57 (e.g. changing mode of operation) of the system, to enable/disable function(s) of the system. For example, an inserter may become operable (e.g. enabling the insertion of a cannula) after validating an ID marker located on a cradle. Additionally and/or alternatively the connection between components may be enabled 61, enabling part replacement.

If the read data is not valid, a notification is provided 55 to the user. The notification typically acknowledges the user about the false/invalid/non-valid reading/information. Then, further reading(s) may be carried out repeatedly (designated as for example by a dotted arrow) or the system operation 59 can be changed upon invalidation. For example, the therapeutic fluid delivery is stopped when the data read from an identification marker located on a cradle is not valid.

It should be noted that in some embodiments some steps may be omitted, such as a notification may not be provided upon invalidation (i.e. omitting step 55), the sequence of steps may be different (e.g. step 57 before step 56), and/or the procedure may include additional steps.

In some embodiments, the database can be updated to comply with the identification tags of different DPs and/or cradle units. For example, if the insulin concentration of the insulin retained in the reservoir has been modified and the insulin concentration is a parameter stored in the ID tag and requires compliance with a validation database, then the validation database can be updated in accordance with the user's insulin concentration requirements. Without update of the validation database, operation of a DP with the various insulin concentrations may not be possible/limited.

According to one such embodiment, the validation database may be accessible for update only by authorized personnel (e.g. physicians, nurses, CDEs, caregivers, parents of diabetic child) using, for example a certain code/password. Update of the validation database can be performed for example via the remote control (RC) that is in communication with the processor using a logon code or via a PC in communication with the processor using a logon code.

If upon a validation procedure the information stored in the identification tag 222 does not match the data of the validation database (e.g. expiry date has elapsed), the processor will not enable operation of the dispensing device. Otherwise, the dispensing device would be operable.

Figure 6:
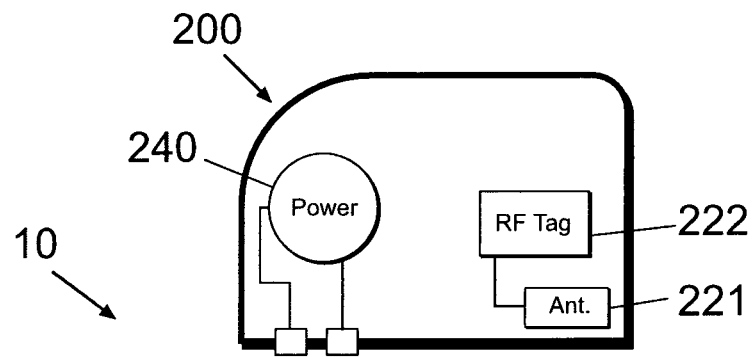
FIG. 6 is a schematic diagram of an RFID-based system that can be used to perform identification and authentication for an insulin dispensing device according to some embodiments of the present disclosure.
Figure 6:
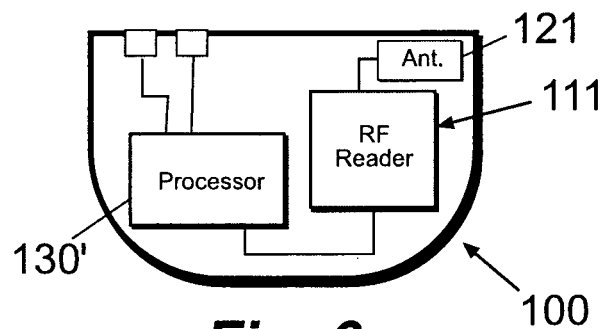

Referring to FIG. 6, a schematic diagram of an RFID-based patch unit 10 to perform identification and/or authentication procedures with respect to its different parts is shown. The RFID-based system comprises an identification tag 222 (RF tag) and a tag antenna 221 that communicates with an identification reader 111 (RF reader) and reader antenna 121 by transmitting, for example, RF signals.

In some embodiments, a carrier signal is generated by the reader 111 (optionally, based on a request from the host computer or processor 130') and sent out (transmitted) throughout the reader antenna 121 to the tag 222 and tag antenna 221. The tag 222 receives the carrier signal and sends/transmits back a modulated signal. The reader antenna 121 receives the modulated signal and sends it to the reader 111. The reader then decodes the data brought by the signal and transfers the results to the processor 130'. In some embodiments, the carrier signal generated by the reader 111 does not convey any information until the data from the tag 222 is added to the signal by modulation and then decoded on the receiving end, i.e. the reader 111, by, for example, performing demodulation operations.

The RFID tag 222 and tag antenna 221 may be located in the DP 200. The reader 111 and reader antenna 121 may be located in the RP 100, which further contains processor 130'. In some embodiments the power supply 240 may reside in the DP 200 of the patch unit 10.

RFID tags are generally available in three varieties: passive, active, or semi-passive. Passive tags require no internal power source, thus being pure passive devices (they are only active when a reader is nearby to energize them). When an electrical current induced in the antenna by an RF signal, a power is provided to an integrated circuit of the ID tag to power it up and thereafter to transmit a response. Passive tags can generally be read by readers located at a relatively short distance.

Active tags require a dedicated power source, usually a small battery, which is used to power the integrated circuits and broadcast the signal to the reader. Active tags are typically much more reliable than passive tags due to the ability of the active tags to interact with a reader (e.g., conduct a "session"). Active tags, due to their onboard power supply, also transmit at higher power levels than passive tags, thus enabling them to be more effective in "RF challenged" environments (i.e. when the Signal-to-Noise (S/N) ratio is low), or at longer distances. Some active RFID tags include sensors such as temperature gauges which can be used for example to monitor the temperature of the patch unit. On the other hand, active tags are generally larger in size and more expensive to manufacture, and their potential shelf life is typically shorter.

Semi-passive tags are similar to active tags in that they have their own power source (e.g., a battery), but they typically do not broadcast communication signals. The RF energy is reflected back to the reader as done by a passive tag. Semi-passive tags have higher sensitivity than passive tags, and longer battery life than active tags.

In some embodiments, the RFID tag may be a passive tag. Use of a passive tag enables tag miniaturization and low cost, and is applicable because the limited read range of the passive tag is not a factor in the current application, due to the small dimensions of the patch unit.

In some embodiments, the RFID tag can be an active tag or semi-passive tag, i.e. it would have its own power source. Such embodiments are feasible because the power supply of the patch unit is preferably located in the DP, and can thus provide the necessary power for the active or semi-passive RFID tag.

In some embodiments, the RFID tag status changes from passive to active or semi-passive, according to the connection condition of the two parts together. For example, an RFID tag located on a cradle is passive until it is connected to a dispensing unit. The passive RFID tag enables the determination of the connection condition between the cradle and the dispensing unit. Thus, drug/fluid delivery is halted when there is no connection and it is resumed when there is a connection. The active status of the RFID tag enables its reading by another unit (e.g. a remote control unit), not connected to it.

In some embodiments, the system can include a disabling mechanism to harm or ruin the RFID tag, making it unreadable during the assembly of the patch unit (i.e. when the RP is being connected to the DP). Rendering the RFID tag unreadable can be done by configuring the RP housing to be pushed against the RFID tag, thus directly damaging its functionality. Alternatively, the RFID tag can be subjected to overload (e.g. relatively high level of electrical power), which may be induced by the RFID reader, and thus melting electrical connectors. Damaging the RFID tag to disable additional readings prevents reusing or undesirable use of a single use part.

Figure 7A:
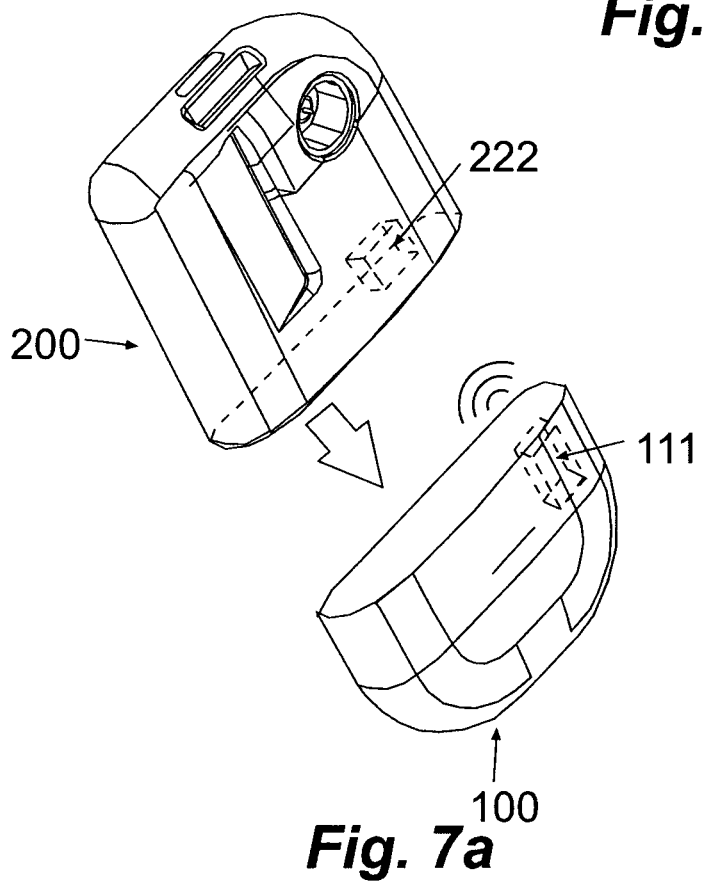
FIGS. 7a-d are views of an exemplary RFID-based identification and authentication system according to some embodiments of the present disclosure.
Figure 7B:
Figure 7C:
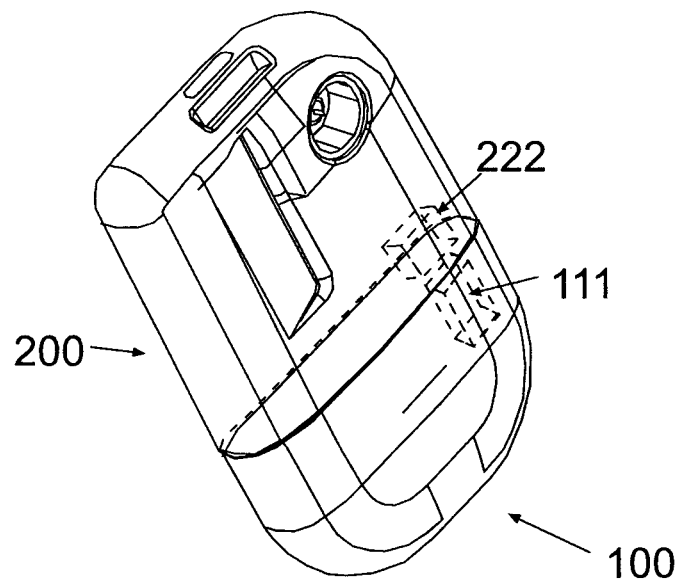
Figure 7D:
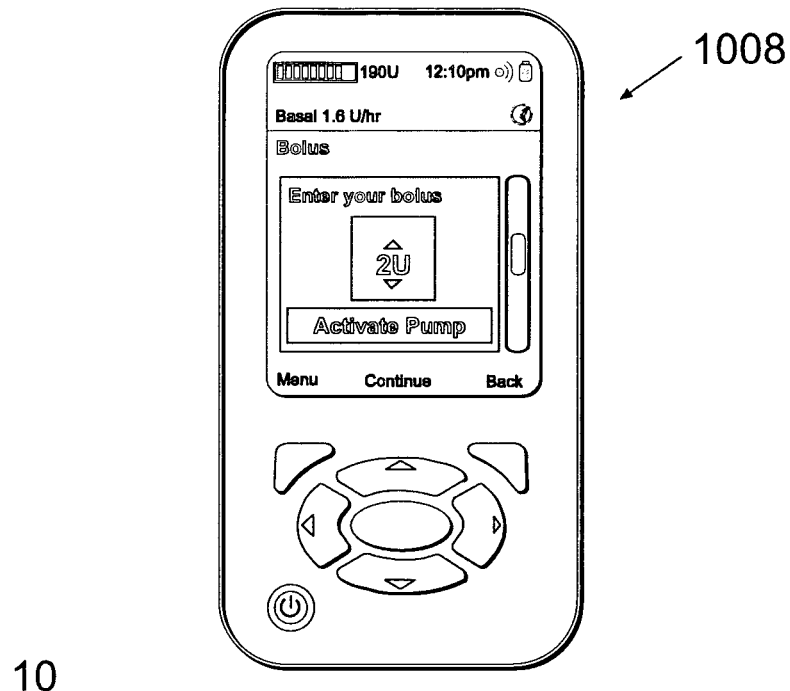

Referring to FIGS. 7a-d, views of exemplary a two-part patch unit with a remote control unit and an RFID-based validation mechanism (e.g., identification and/or authentication system) are shown. FIGS. 7a and 7c depict the disassembled and assembled patch unit, respectively. An RF identification reader 111 is located at the RP 100 and communicates via RF communication with an identification tag 222 located at the DP 200. The identification and authentication approval or rejection can be displayed as a message on a remote control unit's 1008 display (as shown, for example, in FIGS. 7b, 7d), or generated as an audio signal and/or an audio/visual signal, and/or vibrational notification and/or alerting the patient in any other way.

In some embodiments, notification of identification and authentication approval or rejection can be generated directly by the patch unit, for example, by the RP, as an audio signal (e.g., via a buzzer) and/or by vibration and/or as a visual signal displayed on a screen located on the RP, and/or by alerting the patient in any other way.

Figure 8B:
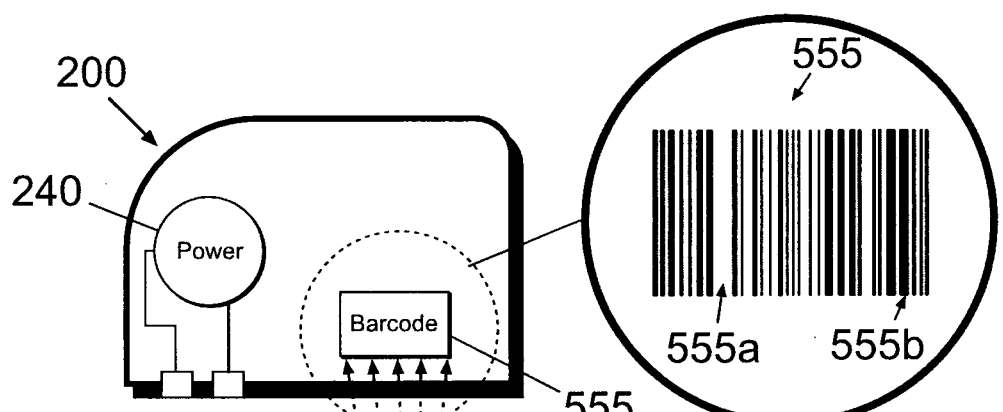
FIGS. 8a-b is a schematic diagram of an exemplary barcode system to perform identification and authentication operations for an insulin dispensing device according to some embodiments of the present disclosure.
Figure 8A:
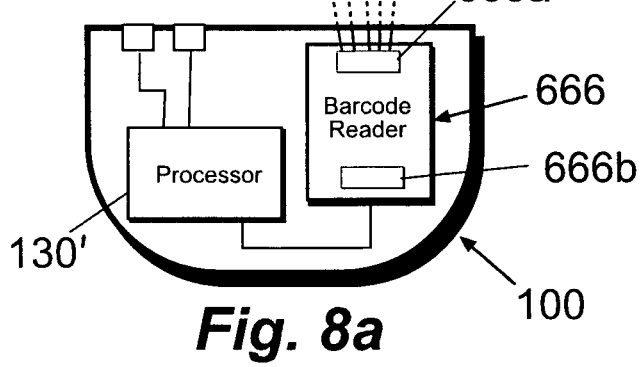

Referring to FIGS. 8a-b, a schematic diagram of an exemplary two-part patch unit with a bar code-based validation mechanism to perform identification and authentication operations with respect to its different parts is shown according to some embodiments.

In such embodiments, the identification tag is configured as a bar code 555 representative of identification information, and which includes a series of parallel, adjacent bars 555b and spaces 555a, as shown in FIG. 8b.

A barcode reader 666 is provided and can decode a bar code by directing, for example, a light source 666a towards the bar code, emitting light (or other form of energy such as IR radiation) and measuring the intensity of light reflected back by the bar code. The pattern of reflected light is detected by a detector 666b (e.g. a photodiode) which produces an electronic signal that corresponds to the detected pattern. This signal is then decoded to retrieve the original data which is then transmitted to the processor 130'. The energy required to power the barcode reader can be provided by a power supply 240.

In some embodiments, the bar code 555 may be located at the DP 200 and/or at the cradle unit. The bar code reader 666 may be located at the RP 100, as well as the processor 130'. The power supply 240 may reside in the DP 200 of the patch unit 10. Alternatively, the power source 240 is located in RP 100 and may be rechargeable.

In some embodiments, the bar code 555 can be harmed or ruined, making it unreadable during the assembly of the patch unit (i.e. when the RP is being connected to the DP). Rendering the bar code unreadable can be done by configuring the RP housing to rub against the bar code. Alternatively, the barcode can be removed by the user. Damaging the bar code to disable additional readings prevents reusing or undesirable use of a single use part.

It should be noted that although the embodiments described refer to a bar code located on a DP, the bar code can be placed on any part of the system. Furthermore, the barcode reader may be located on other parts of the system (e.g. insertion device, remote control unit). In some embodiments, the system can include more than one component having a barcode and/or barcode reader.

Figure 9A:
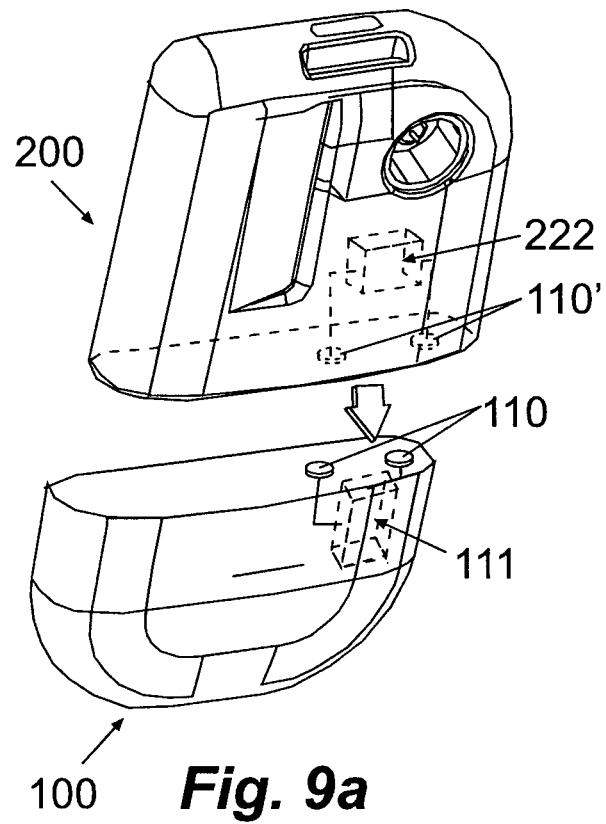
FIGS. 9a-b illustrate views of an exemplary FLASH memory identification and authentication system according to some embodiments of the present disclosure.
Figure 9B:
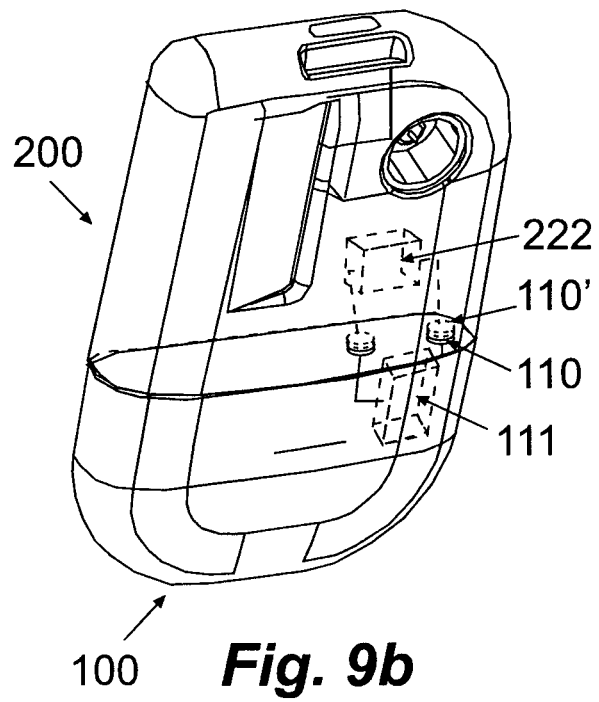

Referring to FIGS. 9a-b, views of an exemplary two-part patch unit with a FLASH memory-based validation mechanism to perform identification and authentication are shown according to some embodiments. The FLASH-based validation system includes a FLASH memory provided at the disposable part 200, which serves as an identification tag 222, and a FLASH reader provided at the RP 100, serving as an identification reader 111. In some embodiments, the FLASH reader is integrated with the dispensing unit processor.

FIG. 9a depicts the disassembled patch unit. The identification reader 111 comprises connectors 110 which, upon connection of the RP to DP (shown in FIG. 9b), contact the corresponding connectors 110' of the identification tag 222 provided at the DP. Once the parts (RP and DP) are physically connected, the identification and/or authentication procedure can be performed.

In some embodiments, a cradle unit (not shown) may also include a FLASH memory identification tag and connectors that contact the corresponding connectors of the identification reader provided at the RP, for example.

The FLASH memory may be any known FLASH chip (commercially available, or otherwise).

In some embodiments, the data stored on the FLASH memory is altered as result of the connection/usage of the part. This enables the tracking of the part's period of usage, the number of connections and disconnections, and thus may prevent reuse or undesirable use of single use parts (e.g. a reservoir, a cannula, a DP, a cradle).

Figure 10:
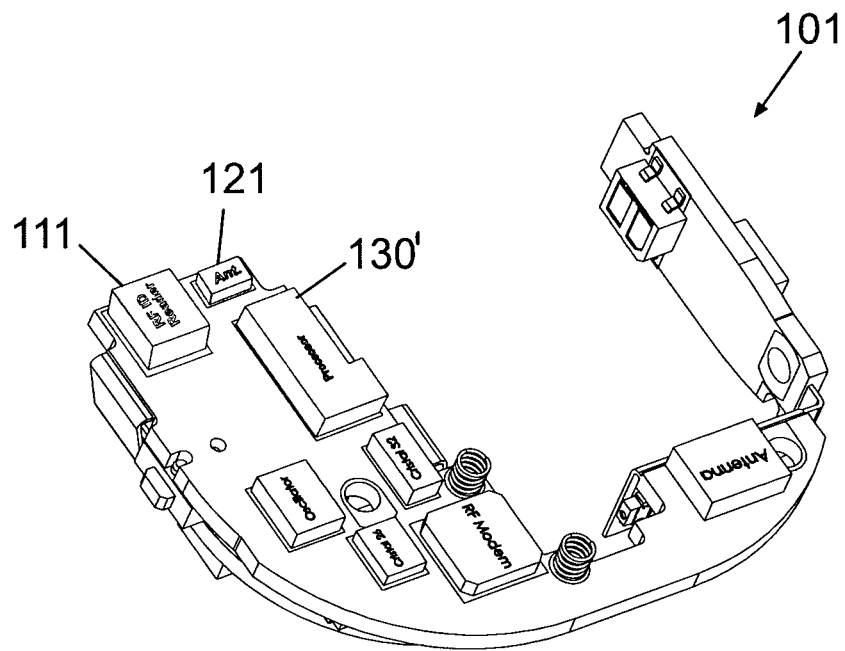
FIG. 10 is perspective view of an exemplary embodiment of a motherboard of the reusable part of a dispensing patch unit that includes an RFID-based identification and authentication system according to some embodiments of the present disclosure.

Referring to FIG. 10, a perspective view of an exemplary embodiment of a Printed Circuit Board (PCB) 101 of the reusable part 100, including the relevant components of an RFID-based validation mechanism to perform identification and authentication is shown. The PCB 101 comprises an RFID reader 111, an RFID reader antenna 121, and a processor 130'. The RFID reader 111 is configured to generate a carrier signal transmitted by antenna 121 to an RFID tag and tag antenna possibly located on other parts of the device, e.g., DP, cradle unit (shown for example in FIG. 11a). A tag modulated signal is subsequently received by the reader antenna 121, forwarded to the RFID reader 111 which can decode the signal and transfer the encoded information/data to the processor 130'.

Figure 11A:
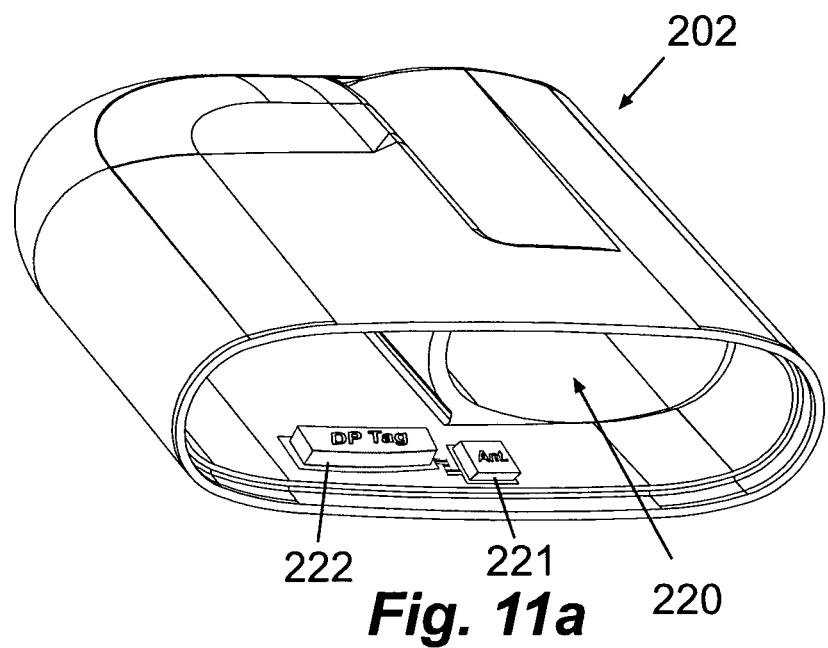
FIGS. 11a-b are views of exemplary embodiments of a dispensing patch unit that includes an RFID-based identification and authentication system according to some embodiments of the present disclosure.
Figure 11B:
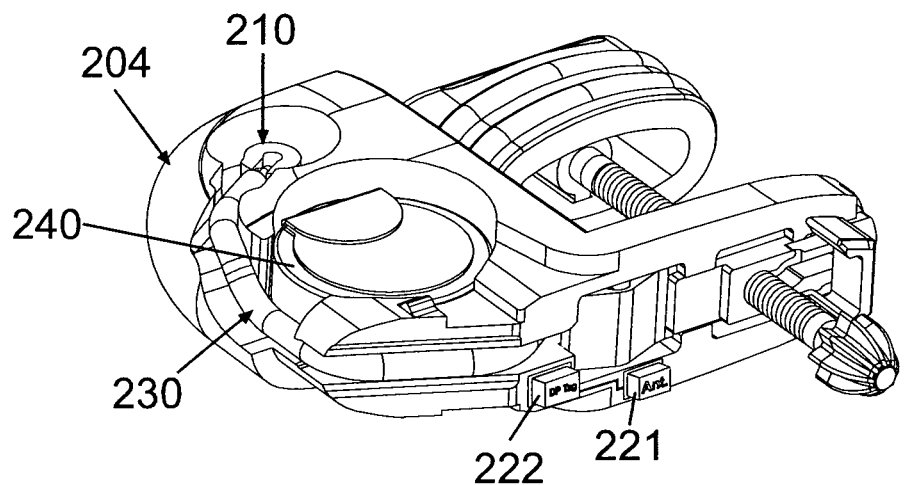

Referring to FIGS. 11a-b, views of exemplary embodiments of the disposable part 200 of a dispensing patch unit with the relevant components of a RFID-based validation mechanism to perform identification and authentication are shown.

As illustrated in FIG. 11a, the RFID tag 222 (also referred-to as "DP Tag") and RFID tag antenna 221 are located on the inner side of the disposable part housing 202. Both the RFID tag 222 and the antenna 221 are positioned adjacent to the reservoir 220 such that there is no interference with the piston and/or fluid delivery when the disposable part and reusable part are connected.

As illustrated in FIG. 11b, the RFID tag 222 and RFID tag antenna 221 are located on the disposable part chassis 204. The chassis 204 may house some of the disposable components such as power supply 240, delivery tube 230 and outlet port 210. The tag 222 and antenna 221 of the DP chassis 204 are positioned so that they are aligned with the RFID reader 111 and antenna 121 of the reusable part 100 to facilitate communication between the components of the RFID-based mechanism.

Figure 12:
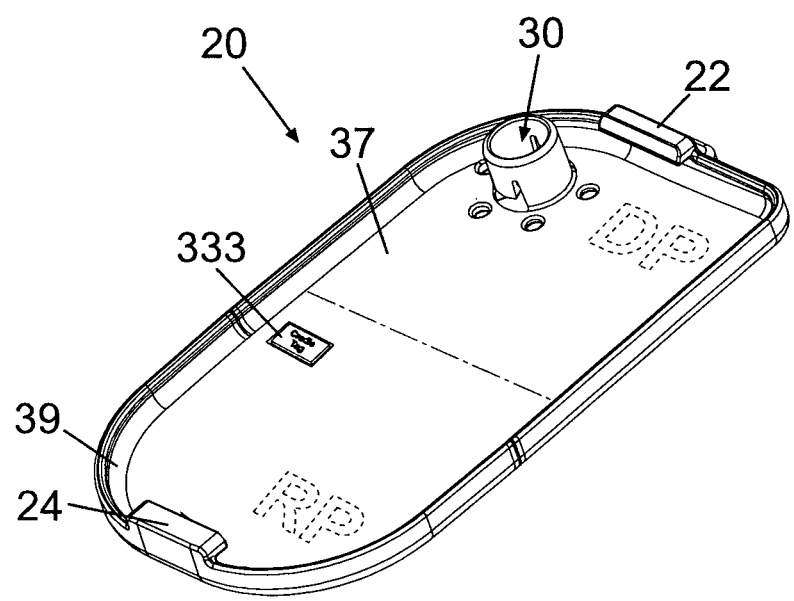
FIG. 12 is a view of an exemplary embodiment of a cradle unit provided with an identification tag according to some embodiments of the present disclosure.

Referring to FIG. 12, a view of an exemplary embodiment of the cradle unit 20 is shown. The cradle unit 20 includes an identification tag 333, a well 30 through which the cannula can be inserted, a base 37, a border 39, and locking mechanisms, which may comprise latches 22, 24 to secure the dispensing unit. In some embodiments, the cradle may include the reservoir and/or the power supply. When the dispensing unit 10 is connected with the cradle 20, the identification tag 333 is identified by an identification reader located at the dispensing unit and thus authentication of the patch unit 10 and cradle unit 20 is possible. As shown, in some embodiments, the tag 333 is positioned in the left corner of the section where the reusable part is supposed to be placed when connecting the dispensing unit 10, so that the identification reader is positioned opposite to the tag 333 enabling uninterrupted communication and identification. In some embodiments, the reader can be positioned in the section where the DP is placed when connected to the cradle.

A number of embodiments have been described. Nevertheless, it will be understood that various modifications may be made to the disclosed embodiments, as well as to the individual features thereof, without departing from the spirit and scope of the present disclosure. For example, the locations of the ID marker and the ID reader each may be located on any portion of the system. In some embodiments, the ID marker may be located on a single use component such as, cannula, cradle, reservoir, tubing, vial for therapeutic fluid, DP, including their packages, covers and the like. In some embodiments, the ID reader may be located on reusable components (i.e. components configured for more than a single usage) and/or component having a prolong lifetime (e.g. months, years), such as remote control unit, dispensing unit, insulin pump, RP and inserter.

The processors described herein may include a controller, a CPU, a MCU, a memory device and/or plurality of such components. The processor device(s) may further include peripheral devices to enable input/output functionality. Alternatively and/or additionally, in some embodiments, special purpose logic circuitry, e.g., an FPGA (field programmable gate array) or an ASIC (application-specific integrated circuit) may be used in the implementation of the processor device(s).

Various embodiments of the subject matter described herein may be realized in digital electronic circuitry, integrated circuitry, specially designed ASICs (application specific integrated circuits), computer hardware, firmware, software, and/or combinations thereof. These various embodiments may include embodiment in one or more computer programs that are executable and/or interpretable on a programmable system including at least one programmable processor, which may be special or general purpose, coupled to receive data and instructions from, and to transmit data and instructions to, a storage system, at least one input device, and at least one output device. In particular, some embodiments include specific "modules" which may be implemented as digital electronic circuitry, integrated circuitry, specially designed ASICs (application specific integrated circuits), computer hardware, firmware, software, and/or combinations thereof.

These computer programs (also known as programs, algorithms, procedures, processes, software, software applications or code) include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

Some or all of the subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an embodiment of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

Some embodiments of the present disclosure preferably implement the identification and/or authentication via software operated on a processor contained in a remote control device of an insulin dispensing system and/or a processor contained in a insulin dispensing device being party of an insulin dispensing system.

Any and all references to publications or other documents, including but not limited to, patents, patent applications, articles, webpages, books, etc., presented in the present application, are herein incorporated by reference in their entirety.

Although a few variations have been described in detail above, other modifications are possible. For example, the logic flow depicted in the accompanying figures and described herein do not require the particular order shown, or sequential order, to achieve desirable results. Other embodiments are possible, some of which, are within the scope of the following claims.

What is claimed is:

1. A system for dispensing insulin into a body of a user, the device system comprising:
    a cradle unit configured to attach to the body of the user;
    a first portion configured for removable attachment to the cradle unit, the first portion having at least a portion of a driving mechanism, a processor and at least one ID reader;
    a second portion having a reservoir and at least one ID marker; and
    a disabling mechanism configured to mechanically disable the at least one ID marker by direct physical contact with the at least one ID marker which damages functionality of the at least one ID marker to render the at least one ID marker unreadable by the at least one ID reader,
    the disabling mechanism operated based on a determination by the processor of the corresponding signal received from the at least one ID reader;
    wherein upon connection of the first portion to the second portion the at least one ID reader reads the at least one ID marker for authenticating the second portion and provides a corresponding signal to the processor as a result of such reading, and
    wherein operation of the system is enabled by the processor based on the corresponding signal confirming authentication of the second portion.

2. The system of claim 1, wherein the second portion further includes a power source, and upon connection of the first portion to the second portion power is provided from the power source to at least the driving mechanism, the processor and the at least one ID reader.

3. The system of claim 1, wherein one or more functions of the system are enabled by the processor based on the corresponding signal, the one or more functions being selected from the group consisting of: inserting a cannula into the body of a user, dispensing a therapeutic fluid to the body of the user, setting an amount of a therapeutic fluid for delivery to the body of the user, replacing a reservoir, assembling a dispensing unit, and stopping a delivery of a therapeutic fluid to the body of the user.

4. The system of claim 1, wherein the first portion is a reusable part and the second portion is a disposable part and configured for removable attachment to the cradle unit.

5. The system of claim 1, wherein the second portion is integral with the cradle unit.

6. The system of claim 1, wherein the system further comprises an inserter configured for inserting a cannula into the body of the user, the inserter including a second ID reader configured for communicating with an ID marker located on the cannula and optionally with the at least one ID marker.

7. The system of claim 1, wherein assembly of the first portion to the second portion changes the at least one ID marker.

8. The system of claim 1, wherein the at least one ID reader includes an RFID reader and the at least one ID marker includes an RFID tag.

9. The system of claim 1, wherein the at least one ID marker includes a rewriteable memory.

10. The system of claim 1, wherein the at least one ID marker includes a barcode and the at least one ID reader includes a barcode reader.

11. The system of claim 1, wherein:
    the system further includes a database for storing information related to reading of the at least one ID marker;
    at least a portion of the corresponding signal received from the at least one ID reader comprises information; and
    the processor compares at least some of the information received from the at least one ID reader with at least some of the information stored in the database.

12. The system of claim 1, wherein the disabling mechanism disables subsequent reading of the at least one ID marker after connection between at least one the first portion of the system with at least one the second portion of the system.

13. The system of claim 1, wherein the disabling mechanism operates to push or rub against the at least one ID maker to mechanically disable the at least one ID marker through direct physical contact with the at least one ID marker.

14. A system for dispensing a therapeutic fluid to a body of a user, the system comprising:
    a cradle unit configured to attach to the body of the user;
    a reservoir for containing the therapeutic fluid;
    a cannula insertable into the body of the user for providing at least a portion of a fluid path between the reservoir and the user's body;
    a driving mechanism configured for removable attachment to the cradle unit, the driving mechanism configured for engaging with the reservoir for dispensing the therapeutic fluid;
    a processor controlling the driving mechanism;
    at least one ID marker for authenticating at least a portion of the system; at least one ID reader for reading the at least one ID marker and for providing a signal to the processor based on such reading; and a power source for providing power to at least one of the driving mechanism, the at least one ID reader and the processor; and a disabling mechanism configured to mechanically disable the at least one ID marker by direct physical contact with the at least one ID marker which damages functionality of the at least one ID marker to render the at least one ID marker unreadable by the at least one ID reader, the disabling mechanism operated based on a determination by the processor of the corresponding signal received from the at least one ID reader;

wherein the processor enables one or more functions of the system based on the signal received from the at least one ID reader.

15. The system of claim 14, wherein the system includes a dispensing unit which includes the reservoir, the driving mechanism and the at least one ID marker, and a remote control unit which includes the at least one ID reader.

16. The system of claim 14, wherein the system comprises at least two portions, a first portion having the at least one ID marker and a second portion having the at least one ID reader, and wherein the first portion further includes at least one of:

a cannula, a reservoir, the cradle, a tubing enabling fluid communication between the reservoir and the cannula, a vial of therapeutic fluid, a connector configured for enabling fluid communication between a vial of therapeutic fluid and the reservoir, and a probe for measuring analyte levels of the user's body.

17. The system of claim 14, wherein the system further comprises a sensor for monitoring analyte levels, wherein the sensor includes a second ID marker and/or a second ID reader.

18. A method for authenticating components of a system for dispensing a therapeutic fluid to body of a user, the method comprising:

providing a system for dispensing a therapeutic fluid to a body of a user, the system having a cradle unit configured to attach to the body of the user, at least one ID marker, at least one ID reader and a processor controlling one or more functions of the system;

reading the at least one ID marker with the at least one ID reader, providing a signal from the at least one ID reader to the processor based on the reading of the at least one ID marker, and enabling the one or more functions of the system according to the signal provided, and disabling the at least one ID marker with a disabling mechanism which is operated based on a determination by the processor of the signal received from the at least one ID reader, wherein the disabling mechanism is configured to mechanically disable the at least one ID marker by direct physical contact with the at least one ID marker which damages functionality of the at least one ID marker to render the at least one ID marker unreadable by the at least one ID reader.

19. The method of claim 18, further comprising limiting the one or more functions based on the signal.

* * * * *

UNITED STATES PATENT AND TRADEMARK OFFICE
CERTIFICATE OF CORRECTION

PATENT NO. : 9,138,531 B2
APPLICATION NO. : 12/995068
DATED : September 22, 2015
INVENTOR(S) : Ofer Yodfat et al.

It is certified that error appears in the above-identified patent and that said Letters Patent is hereby corrected as shown below:

Specification

Col. 1, Line 66,
"infusion set are rejected by the majority of diabetic insulin" should read
--infusion sets are rejected by the majority of diabetic insulin--;

Col. 4, Line 5,
"communicate with the patch unit and may be enable its pro-" should read
--communicate with the patch unit and may enable its pro- --;

Col. 5, Line 32,
"the identification reading (e.g. using parts form different" should read
--the identification reading (e.g. using parts from different--;

Col. 5, Line 51,
"tication the different parts of the device/system before and/or" should read
--tication of the different parts of the device/system before and/or--;

Col. 6, Line 3,
"and a mechanical reader. The mechanicals reader and identi-" should read
--and a mechanical reader. The mechanical reader and identi- --;

Col. 10, Line 20,
"tication and/or the identification status (e.g. if the reading are" should read
--tication and/or the identification status (e.g. if the readings are--;

Col. 13, Line 19,
"these circumstance, if the key of one part mechanically fits" should read
--these circumstances, if the key of one part mechanically fits--;

Signed and Sealed this
Thirty-first Day of May, 2016

Michelle K. Lee
*Director of the United States Patent and Trademark Office*

CERTIFICATE OF CORRECTION (continued)
U.S. Pat. No. 9,138,531 B2

Col. 13, Line 53,
"replacing a reservoir), periodically, and when other operation" should read
--replacing a reservoir), periodically, and when other operations--;

Col. 18, Line 11,
"component having a prolong lifetime (e.g. months, years)," should read
--component having a prolonged lifetime (e.g. months, years),--;

Col. 19, Line 26,
"processor contained in a insulin dispensing device being party of an" should read
--processor contained in an insulin dispensing device being party of an--;

Claims

Col. 20, Claim 12, Lines 45-46,
"marker after connection between at least one the first portion of the system with at least one the second portion of the" should read
--marker after connection between at least one of the first portion of the system with at least one of the second portion of the--; and Col. 20, Claim 13, Line 49,
"nism operates to push or rub against the at least one ID maker" should read
--nism operates to push or rub against the at least one ID marker--.